(12) United States Patent
Moreau et al.

(10) Patent No.: US 11,820,686 B2
(45) Date of Patent: Nov. 21, 2023

(54) BIOELECTROCHEMICAL REACTOR WITH DOUBLE BIOANODE, METHOD FOR ANODIC REGENERATION AND USE OF THE REACTOR FOR MICROBIAL ELECTROSYNTHESIS

(71) Applicants: CENTRE NATIONAL DE LA RECHERCHE SCIENTIFIQUE, Paris (FR); INSTITUT NATIONAL POLYTECHNIQUE DE TOULOUSE, Toulouse (FR); INSTITUT NATIONAL DE RECHERCHE POUR L'AGRICULTURE, L'ALIMENTATION ET L'ENVIRONNEMENT, Paris (FR); SUEZ Groupe, Paris la Défense (FR)

(72) Inventors: Sylvain Moreau, Sucy en Brie (FR); Théodore Bouchez, Villemoisson (FR); Jianghao Tian, Massy (FR); Elie Le Quemener, Narbonne (FR); Alain Bergel, Toulouse (FR); Elise Blanchet, Bourg St Bernard (FR); Benjamin Erable, Giroussens (FR); Luc Etcheverry, Montlaur (FR); Alain Huyard, Les Mureaux (FR); Pierre Mauricrace, Grandchamp (FR); Nicolas Bernet, Cuxac d'Aude (FR); Eric Trably, Cuxac d'Aude (FR)

(73) Assignees: CENTRE NATIONAL DE LA RECHERCHE SCIENTIFIQUE, Paris (FR); INSTITUT NATIONAL POLYTECHNIQUE DE TOULOUSE, Toulouse (FR)

( * ) Notice: Subject to any disclaimer, the term of this patent is extended or adjusted under 35 U.S.C. 154(b) by 404 days.

(21) Appl. No.: 17/274,308

(22) PCT Filed: Sep. 12, 2019

(86) PCT No.: PCT/FR2019/052110
§ 371 (c)(1),
(2) Date: Mar. 8, 2021

(87) PCT Pub. No.: WO2020/053529
PCT Pub. Date: Mar. 19, 2020

(65) Prior Publication Data
US 2021/0340039 A1    Nov. 4, 2021

(30) Foreign Application Priority Data
Sep. 13, 2018    (FR) .................................. 18 58240

(51) Int. Cl.
*C02F 3/00*    (2023.01)
*C12P 7/02*    (2006.01)
(Continued)

(52) U.S. Cl.
CPC ............... *C02F 3/005* (2013.01); *C12P 7/02* (2013.01); *C25B 3/23* (2021.01); *C25B 3/25* (2021.01);
(Continued)

(58) Field of Classification Search
None
See application file for complete search history.

(56) References Cited

U.S. PATENT DOCUMENTS

| 2009/0317882 A1* | 12/2009 | Cheng | ..................... C12P 5/023 435/243 |
| 2010/0270158 A1* | 10/2010 | Logan | ..................... C02F 1/469 204/632 |

(Continued)

FOREIGN PATENT DOCUMENTS

CN    103 922 487    6/2016

OTHER PUBLICATIONS

Kong et al. (Bioresource Technology, 2014, 151, 332-339). (Year: 2014).*
(Continued)

*Primary Examiner* — Clare M Perrin
(74) *Attorney, Agent, or Firm* — IPSILON USA, LLP

(57) ABSTRACT

A bioelectrochemical reactor (1) has an anode chamber (11) having at least two bioanodes (12, 13), and an anodic
(Continued)

electrolyte (14) with an anodic electroactive microorganisms,—a cathode chamber (21) with at least one biocathode (22), and a cathodic electrolyte (24) with a cathodic electroactive microorganisms. The anode chamber (11) is separated from the cathode chamber (21) by, running from the anode chamber to the cathode chamber, a cation exchange membrane (31) and an anion exchange membrane (32). The cation and anion exchange membranes are separated from each other by an inter-membrane chamber (30), and means for applying a potential difference between the interconnected bioanodes and the biocathode/biocathodes. The bioanodes and biocathode/biocathodes have active surfaces such that the total active surface of the biocathode/biocathodes (22) is greater than the total active surface of the two bioanodes (12, 13). The arrangement includes a method for regenerating the activity of the bioanodes of the reactor and to the use of said reactor for the electrosynthesis of organic acids and/or alcohols from organic waste.

16 Claims, 5 Drawing Sheets

(51) Int. Cl.
*C25B 3/23* (2021.01)
*C25B 3/25* (2021.01)
*C25B 9/63* (2021.01)
*C25B 11/043* (2021.01)
*C02F 1/461* (2023.01)
*H01M 8/16* (2006.01)

(52) U.S. Cl.
CPC .............. *C25B 9/63* (2021.01); *C25B 11/043* (2021.01); *C02F 2001/46152* (2013.01); *C02F 2209/02* (2013.01); *C02F 2209/06* (2013.01); *C02F 2209/42* (2013.01); *H01M 8/16* (2013.01)

(56) References Cited

U.S. PATENT DOCUMENTS

| | | |
|---|---|---|
| 2014/0069806 A1 | 3/2014 | Silver et al. |
| 2018/0166760 A1* | 6/2018 | Santoro ............... H01M 4/9008 |
| 2019/0161869 A1 | 5/2019 | Bisselink |
| 2020/0010345 A1* | 1/2020 | Ortiz Diaz-Guerra ..................... C02F 1/4693 |

OTHER PUBLICATIONS

Korneel Rabaey et al: "Microbial electrosynthesis—revisiting the electrical route for microbial production", Nature Reviews Microbiology, vol. 8, No. 10, Oct. 1, 2010.

Anonymous: "Auxiliary electrode—Wikipedia", Sep. 8, 2018 (Sep. 8, 2018).

International Search Reports dated Jan. 3, 2020.

* cited by examiner

BIOELECTROCHEMICAL REACTOR WITH DOUBLE BIOANODE, METHOD FOR ANODIC REGENERATION AND USE OF THE REACTOR FOR MICROBIAL ELECTROSYNTHESIS

RELATED APPLICATION

This application is a National Phase of PCT/FR2019/052110 filed on Sep. 12, 2019, which claims the benefit of priority from French Patent Application No. 18 58240, filed on Sep. 13, 2018, the entirety of which are incorporated by reference.

FIELD OF THE INVENTION

The present invention relates to the bioelectrochemical field, and relates more particularly to electrochemical synthesis systems and methods implementing bioelectrochemical reactors, i.e. electrochemical devices in which at least one of the electrodes, called a bioelectrode, is in contact with microorganisms.

PRIOR ART

These bioelectrochemical synthesis devices make it possible in particular, on the basis of organic waste, to produce organic molecules such as organic acids and/or alcohols.

In particular, such a bioelectrochemical device has recently been developed which comprises both a bioanode and a biocathode, both the electrolyte of the anode compartment and the electrolyte of the cathode compartment containing microorganisms in suspension or in the form of one or more biofilms (WO2016/051064). In this device, the activity of the biocathode is optimized with a view to producing particular chemical species in the electrolyte, such as acetic, lactic and/or propionic acids or alcohols. These syntheses of organic molecules by microbial route, involving in particular electrochemical oxidation-reduction reactions, are performed by virtue of electroactive bacteria present on the surface of the electrode.

One of the current problems to be addressed is that of improving the reliability and durability of these bioelectrochemical devices, with a view to applications on an industrial scale.

More particularly, in the device mentioned, one of the objectives is to increase the durability of the bioanode, i.e. to maintain its performance (characterized by acceptable yields in particular in an industrial context) over longer periods. Specifically, it has been observed that the activity of this bioanode decreases considerably after a few weeks of operation. This phenomenon has been defined as the "aging" of the bioanode, probably due to clogging of the biofilm on this electrode. Specifically, a biofilm composed of electroactive bacteria (in particular of the *Geobacter* genus) is necessary for the functioning of the bioanode. Other, non-electroactive microorganisms also grow on this biofilm and thus inhibit its electrocatalytic activity. The deposition of insoluble particles further aggravates this effect.

Furthermore, there is a need for devices and methods that can be deployed on an industrial scale, i.e. they can treat effluent volumes such as those treated today on an industrial scale. Specific problems arise when increasing the size of reactors in order to maintain the levels of activity observed in the laboratory: in particular, the volume of the reactor generally increases more substantially than the active area of the electrodes. In addition, given the operating ranges of microbial electrochemical cells, it is important for the cell to allow the potential of the anode to be controlled with sufficient precision.

This problem is mentioned in particular by Logan et al (Environ. Sci. Technol. Lett. 2015, 2, 206-214), who recommend maintaining a reactor volume/cathode area ratio in order to overcome this problem. However, Logan et al. do not propose any materials or particular configuration for the cathode.

Another objective is to improve the stability of the biocathode.

Cheng et al. (*Environ. Sci. Technol.* 2006, 40, 5426-2432) propose optimizing the generation of the current by varying the distance between the electrodes. In their system the two electrodes are made of carbon fabrics.

However, Cheng et al. propose a microbial fuel cell (MFC) system with a single chamber that contains an abiotic Pt/C cathode. Their study focuses on the generation of electricity by oxidation of glucose at the anode.

The prior art described above does not propose solutions to the specific problems of bioelectrochemical reactors comprising both a bioanode and a biocathode.

AIMS OF THE INVENTION

A first aim of the invention is therefore to overcome the drawbacks of the prior art by proposing a bioelectrochemical reactor, in particular in a bioelectrochemical synthesis device, and a system ensuring that it operates as stably as possible, and over long periods.

Another aim of the invention is to propose a bioelectrochemical reactor whose structure allows the regeneration or restoration of the electrochemical activity of an "aging" bioelectrode, without stopping the operation of the synthesis device.

DESCRIPTION OF THE INVENTION

To this end, the present invention relates to a bioelectrochemical reactor comprising
- an anode compartment comprising at least two anodes, called bioanodes, and an anode electrolyte comprising anodic electroactive microorganisms,
- a cathode compartment comprising at least one cathode, called a biocathode, and a cathode electrolyte comprising cathodic electroactive microorganisms,
- the anode compartment being separated from the cathode compartment by, running from the anode compartment to the cathode compartment, a cation exchange membrane and an anion exchange membrane, said cation and anion exchange membranes being separated from one another by an inter-membrane compartment,
- means for applying a potential difference between the bioanodes connected to one another and the one or more biocathodes,
- the bioanodes and one or more biocathodes having active areas such that the total active area of the one or more biocathodes is greater than the total active area of the at least two bioanodes.

Within the meaning of the invention, a "bioelectrode" ("bioanode" or "biocathode") is an electrode covered, at least partly, with a bacterial biofilm comprising electroactive organisms, i.e. covered, at least over part of its area immersed in the electrolyte, with a bacterial biofilm. According to one embodiment, the entirety of the immersed area of the bioelectrode is covered with biofilm. Alternatively, according to another embodiment, only part of the area of the bioelectrode is covered with biofilm. In this last embodiment, the area covered with biofilm is sufficient to generate the desired activity, in particular in the case of oxidation of organic waste hydrolysates or of bioelectrochemical synthesis.

According to one advantageous embodiment of the invention, the bioelectrochemical reactor comprises two bioanodes and one biocathode. However, the invention may relate to any bioelectrochemical reactor comprising more than two bioanodes and a plurality of biocathodes.

The presence of two bioanodes in the anode compartment allows in particular their use in alternation: in particular, when one is "aging", i.e. when its electrochemical activity decreases, this allows it to be replaced or regenerated. In normal operation, the two bioanodes are electrically connected, generally in parallel. According to one embodiment, these two bioanodes are substantially at the same potential, in particular when their geometry is identical.

The inter-membrane compartment is able to collect the ions or molecules produced in the anode and/or cathode compartments.

What is meant by active area of a bioelectrode (here bioanode or biocathode) is the area exposed to the electrolyte, this area being polarized. According to the invention, the biocathode has greater inertia due to an active area greater than the total active area of the two bioanodes, which makes it possible to ensure a particularly stable cathode potential. Specifically, in operation, once the cathode has reached its working potential, the great stability of the potential of the cathode makes it possible, in practice, to better control the anode potential by varying the potential difference between the biocathode and the bioanodes, and without having to use a reference electrode. Such a system thus allows fine control of the anode potential and therefore optimization of the activity of the anode biofilm.

Advantageously, the bioanodes are removable, and are thus able to be regenerated separately and/or replaced. As a variant, the bioanodes are not necessarily removable and may be regenerated according to the methods described in the parallel applications filed on the same day as the present patent application, under the priority of French applications FR 18 58236 and FR 18 58238, which have not yet been published.

According to one particular embodiment, the bioelectrochemical reactor is a microbial electrosynthesis reactor. In this embodiment, the reactor is characterized in that the anode compartment comprises one or more ports for injecting organic carbonaceous substrate, such as organic biowaste hydrolysates, the cathode compartment comprises one or more ports for injecting $CO_2$ or for introducing an organic or inorganic carbon source and the inter-membrane compartment comprises a device for extracting the molecules synthesized within said reactor.

Regarding the bioelectrodes:
the biocathode is, preferably, a three-dimensional electrode, in particular comprising a granular material or taking the general form of a lattice. The biocathode may, for example, comprise carbon grains arranged in a container made of stainless steel.
the bioanodes preferably take the general form of a panel, in particular a planar or rounded panel. The bioanodes are, for example, formed of a carbon fabric or felt, held in a metal frame, preferably a frame made of stainless steel.

What is meant here by three-dimensional electrode is an electrode whose geometric dimensions of thickness/height/width are such that its thickness corresponds to its smallest dimension and is greater than or equal to ¹⁄₁₀ of each of its other two dimensions. By contrast, the general form of a "panel" is understood to mean an electrode having a thickness of less than ¹⁄₁₀ of each of its other two dimensions, height and width.

Electroactive microorganisms are microorganisms capable of interacting directly with an electrode; here they are typically anaerobic microorganisms. The microorganisms differ depending on the electrode on which they grow as a biofilm, and the characteristics of the electrolyte in which they are immersed. For example, when wastewater or biowaste hydrolysates are injected into the anode electrolyte, an abundant population affiliated with the *Geobacter* genus is observed. Conversely, in a saline environment, other genera such as *Geoalkalibacter* or *Desulforomonas* may become dominant. Thus, when the microorganisms are located on the anode, they are referred to as anodic electroactive microorganisms, while when the microorganisms are located on the cathode, they are referred to as cathodic or electrotrophic electroactive microorganisms.

The reactor, according to the invention, may further comprise means for regulating the pH, the temperature, and/or the electrolyte level, preferably in each of the anode and cathode compartments.

The present invention also relates to a method for regenerating the activity of the bioanodes of the reactor, such as described above, comprising:
a step of removing at least one of the bioanodes from the anode compartment, it being understood that at least one bioanode is left in the anode compartment, and
a step of introducing at least one anode not colonized by electroactive microorganisms into the anode compartment, the reactor being kept in operation by applying a potential difference between the biocathode and the remaining bioanode in the anode compartment.

According to a first embodiment, the non-colonized anode is the anode removed from the compartment, having undergone cleaning. In this embodiment, the method therefore comprises:
a step of removing at least one of the bioanodes from the anode compartment, it being understood that at least one bioanode is left in the anode compartment,
a step of (mechanically, chemically or thermally) cleaning, outside the reactor, said removed bioanode, then reintroducing it into the anode compartment, the reactor being kept in operation by applying a potential difference between the biocathode and the remaining bioanode in the anode compartment.

According to another embodiment, the anode not colonized by electroactive microorganisms is a new anode. According to this embodiment, the method for regenerating the activity of the bioanodes of the reactor, such as described above, comprises replacing one of the bioanodes of the anode compartment with an anode not colonized by electroactive microorganisms, such as a "new" anode, the reactor being kept in operation by applying a potential difference between the biocathode and the remaining bioanode in the anode compartment.

The reactor according to the invention thus allows the regeneration or restoration of "aging" anode electrochemical activity, without stopping the operation of said reactor.

The reactor according to the present invention is advantageously used for the electrosynthesis of organic acids and/or alcohols from organic waste.

The organic waste used in the invention is typically chosen from: biowaste hydrolysates, hydrolyzed sludge from wastewater treatment plants, various organic liquid fractions from wastewater treatment plants, municipal wastewater after primary settling, organic industrial waste, agro-food waste, digestates from wastewater treatment plants, or a mixture of a plurality of the above substrates.

The electrolyte of the anode compartment thus contains such organic carbonaceous substrates in liquid form, introduced either raw or diluted in a synthetic-based electrolyte. In this anode compartment, the organic matter content quantified by measuring the COD (chemical oxygen demand) is advantageously between 0.01 and 200 g/L, preferably between 0.1 and 20 g/L, more preferably between 0.1 and 5 g/L.

The biocathode is advantageously conditioned by introducing an inoculum into the cathode electrolyte.

In one preferred embodiment, the inoculum is prepared from an anaerobic digester sludge, optionally having undergone a pretreatment aimed at inactivating methanogenic microorganisms. Thus, this digester sludge may undergo a heat treatment at a temperature and for a period sufficient for the inactivation of methanogenic microorganisms.

The pretreatment may also comprise the enrichment of the waste with microorganisms of interest. This step may in particular comprise the addition of hydrogen and carbon dioxide, for example in a closed flask in batch mode. For the purposes of the invention, the microorganisms of interest are the microorganisms responsible for bioelectrosynthesis, and comprise for example bacteria capable of using the electrons or hydrogen generated at the cathode to synthesize the desired compounds (such as organic acids or alcohols).

The culture resulting from this enrichment may be used directly and introduced into the cathode compartment upon starting the reactor.

The electrolyte of the cathode compartment contains an electrolyte and a carbon source, injected in the form of gas: such as $CO_2$, biogas, or syngas, and/or introduced in solution in the form of organic carbon: for example acetate, and/or in the form of inorganic carbon: for example a bicarbonate.

BRIEF DESCRIPTION OF THE FIGURES

Other features and advantages of the invention will become apparent from the description below of non-limiting exemplary embodiments, with reference to the appended diagrams, in which.

EXAMPLES

Figure 1:
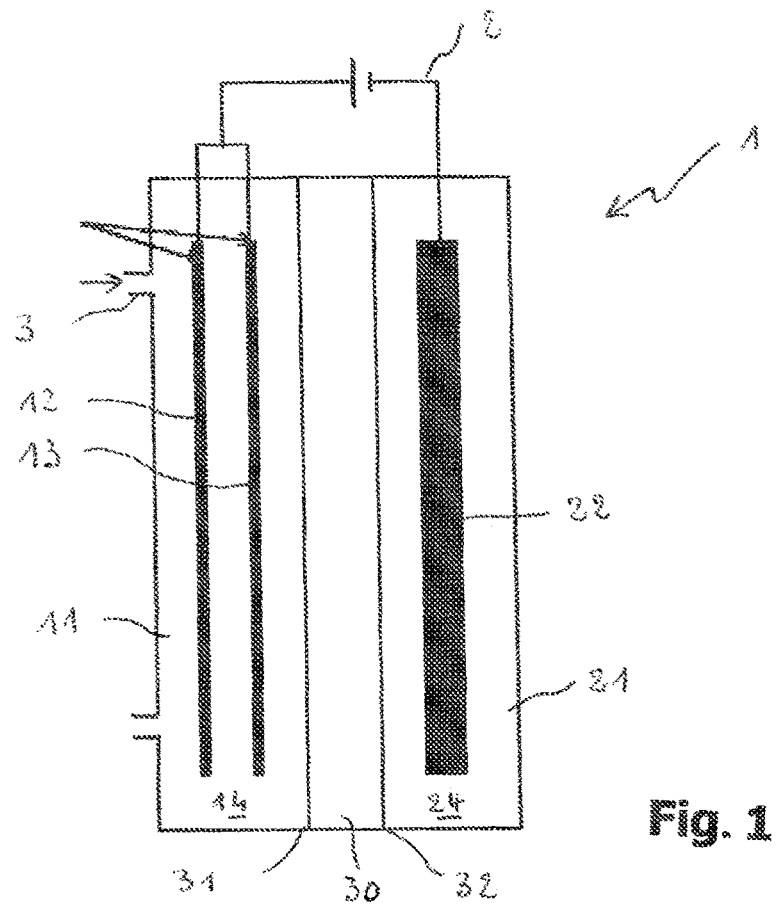
FIG. 1 is a diagram of a bioelectrochemical reactor, according to the invention, showing the various compartments and the location of the bioelectrodes.

With reference to the figures, the reactor according to the invention generally consists of three compartments separated by ion exchange membranes, namely: an anode compartment 11 containing two bioanodes 12 and 13 that are electrically connected to the outside the reactor, and a cathode compartment 21 comprising the biocathode 22, an anode compartment 11 being separated from the cathode compartment 21 by an inter-membrane compartment 30.

A cation exchange membrane 31 separates the anode compartment 11 from the inter-membrane compartment 30 and an anion exchange membrane 32 separates the cathode compartment 21 from the inter-membrane compartment 30.

The anode compartment 11 contains an anode electrolyte 14 comprising anodic electroactive microorganisms. The cathode compartment 21 contains a cathode electrolyte 24 comprising cathodic electroactive microorganisms.

A potential difference 2 is applied between the biocathode 22 and the two bioanodes 12 and 13. The anode compartment comprises in particular a port 3 for injecting organic carbonaceous substrate.

Figure 2:
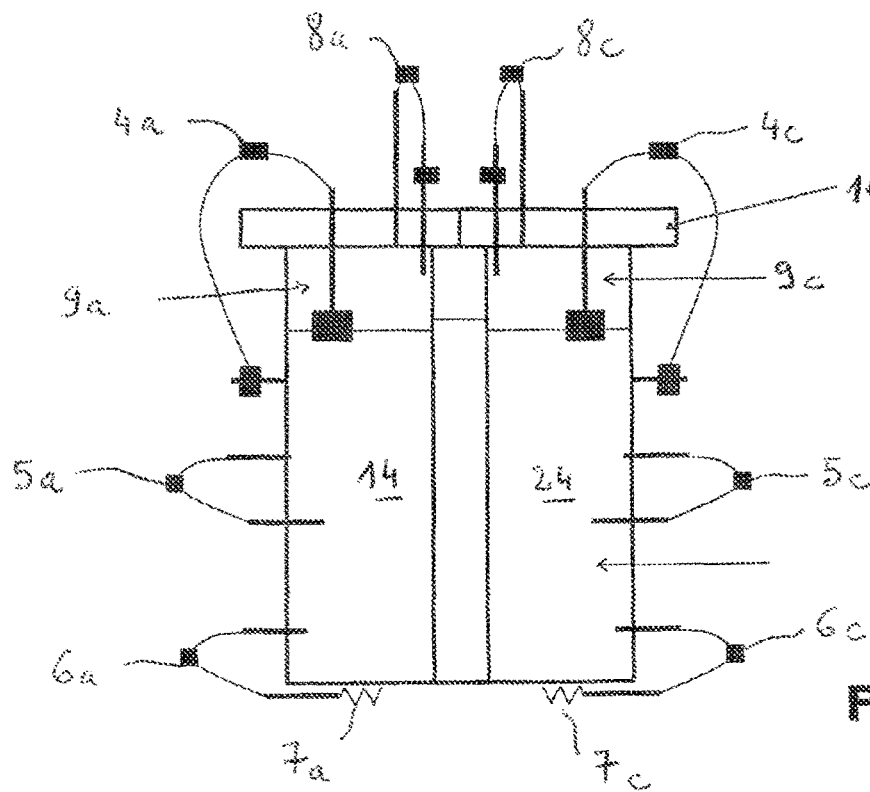
FIG. 2 is a diagram showing the possible regulation systems present in a reactor according to the invention (the electrodes not being shown for greater clarity)

Various regulation systems, in said reactor according to the invention, may be incorporated into said reactor and are shown diagrammatically in FIG. 2. It is possible to have, in particular, a system for regulating the level of the anode liquid 4a and/or cathode liquid 4c, a system for regulating the anode pH 5a and/or cathode pH 5c, a system for regulating the temperature of the anode compartment 6a and/or of the cathode compartment 6c by means, for example, of a heating resistor 7a and/or 7c. Finally, a system for regulating the pressure of the gas phase 9a or 9c may be provided in each of the electrode, i.e. anode 8a or cathode 8c, compartments. Indeed, the reactor is closed by a cover 10.

Figure 3:
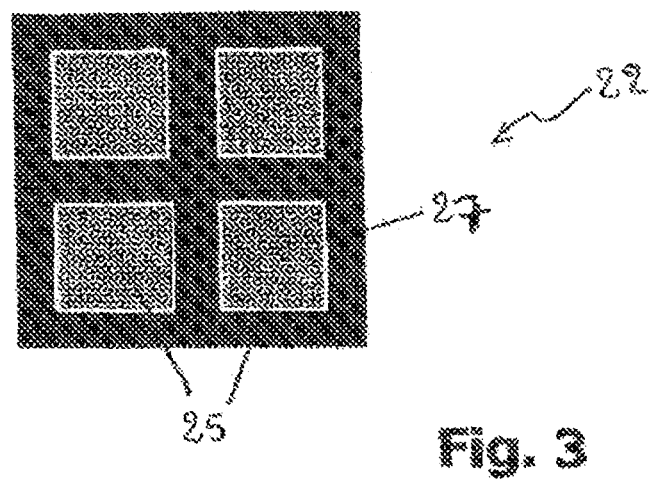
FIG. 3 is a front view of the biocathode, FIG. 3A being a profile diagram of the biocathode of FIG. 3.
Figure 3A:
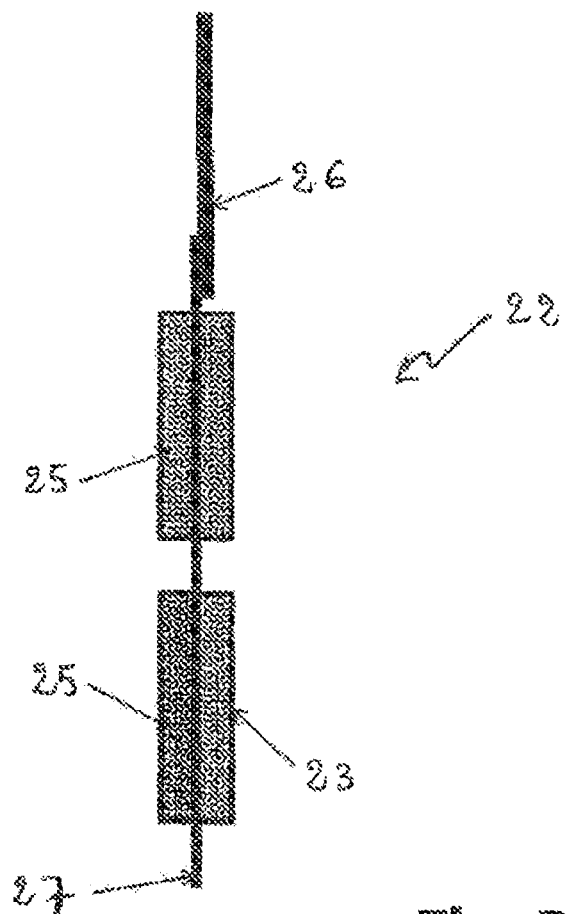

One example of the structure of the cathode is shown in FIGS. 3 and 3A.

The biocathode 21 consists of a frame 27 with a size of 30×30 cm defining four housings in the example presented here. These housings incorporate metal baskets 23 with a thickness of between 4 and 5 cm in which carbon granules 25 are placed. The metal frame 27 is connected to a current collector 26 surmounting said frame.

Figure 4:
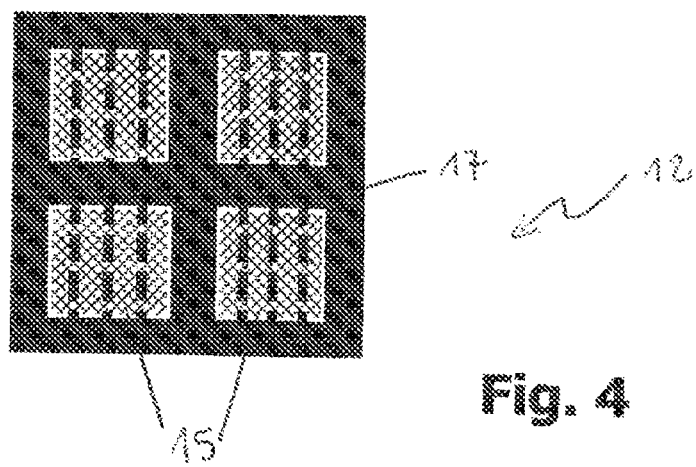
FIG. 4 is a front view of a bioanode, FIG. 4A being a profile diagram of said bioanode of FIG. 4.
Figure 4A:
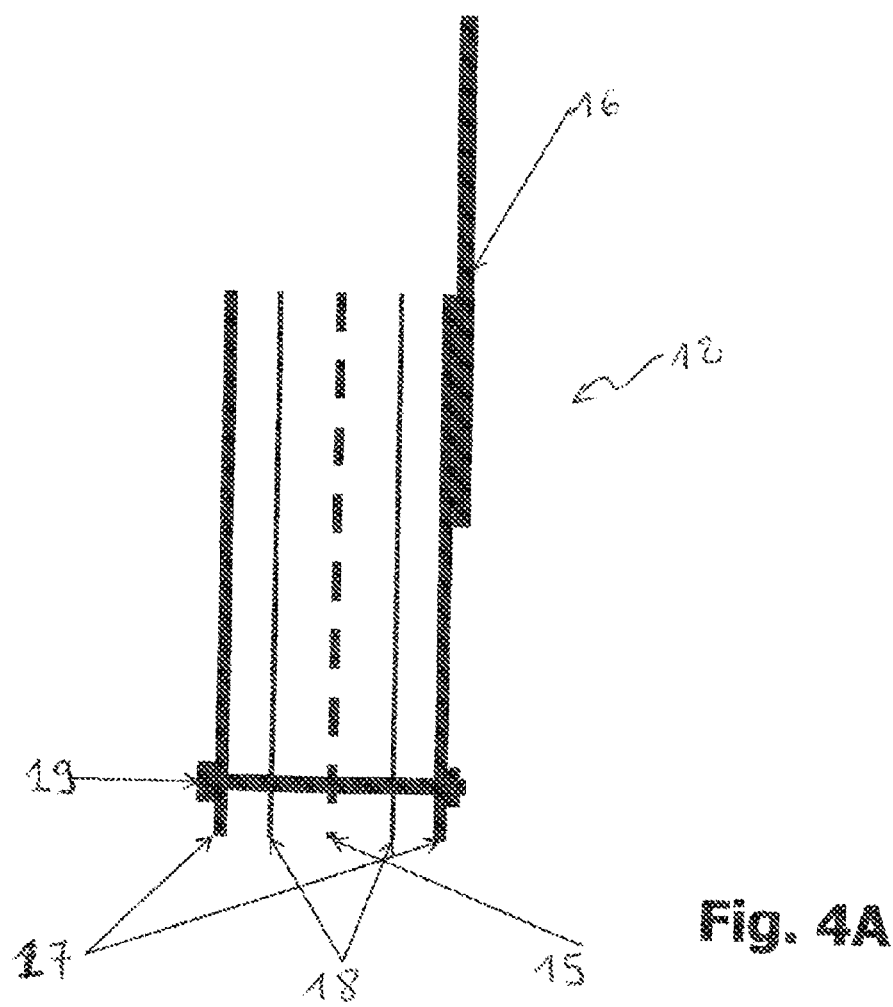

One example of the structure of a bioanode is shown in FIGS. 4 and 4A (exploded view).

For example, the bioanode 12 consists of a metal frame 17 formed of two parallel walls which between them enclose two parallel stainless steel grids 18 housing a carbon fabric 15 between them. This carbon fabric 15 may take the form of a single element or the form of strips of fabric arranged in parallel as shown schematically in FIG. 4. The assembly is held together, for example, by means of bolts 19.

Figure 6:
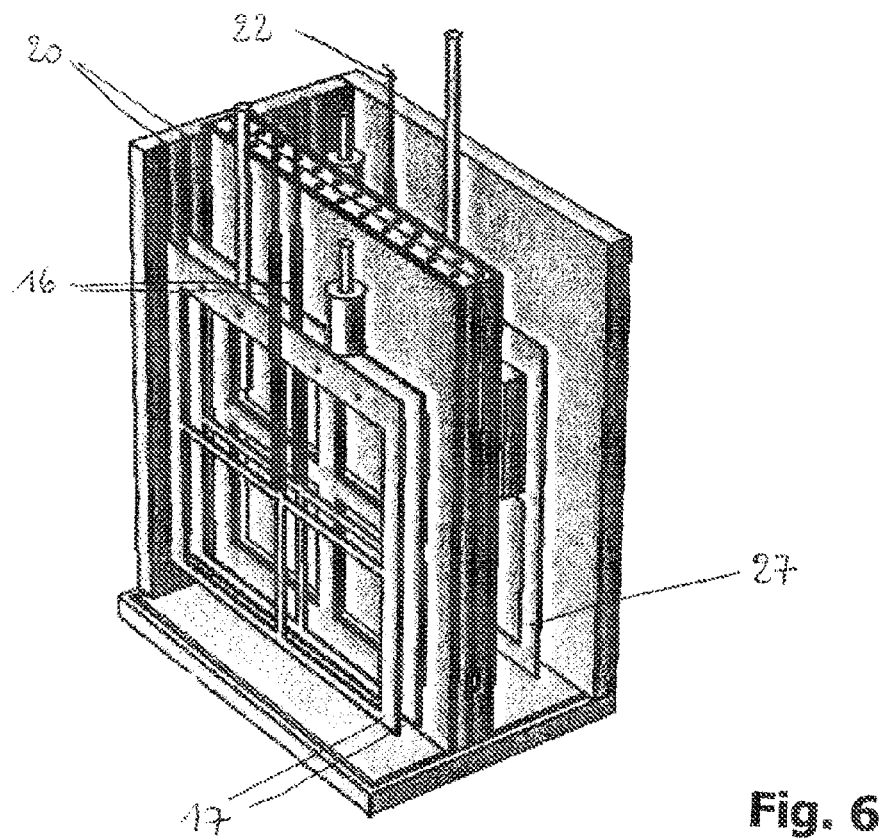
FIG. 6 shows the interior of the compartments of the reactor of FIG. 5.
Figure 7:
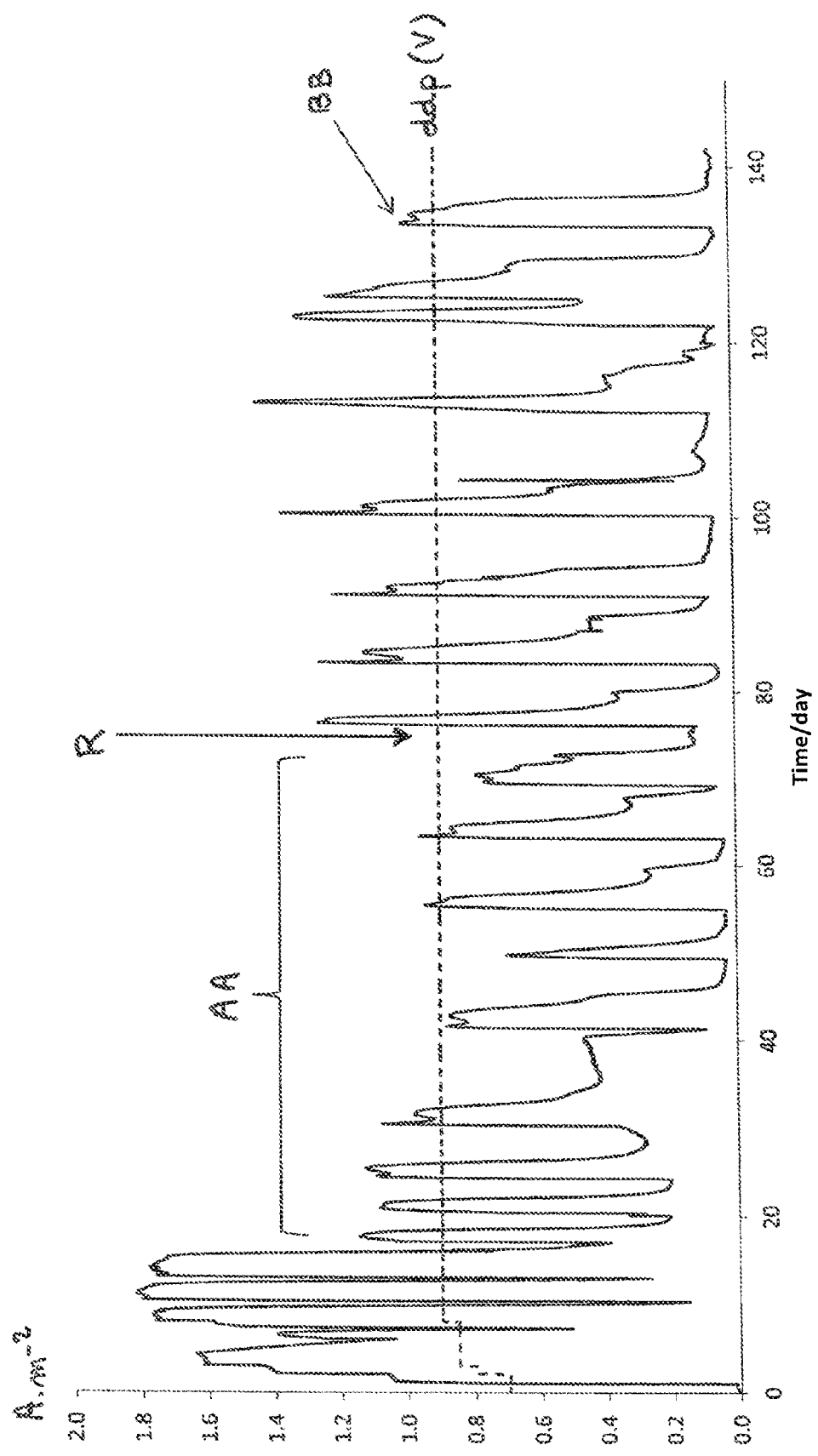
FIG. 7 presents a graph showing the anodic current density of the reactor of FIG. 5, as a function of time, before and after regeneration of one of the bioanodes of the anode compartment.

A more precise description of the bioelectrochemical reactor 1 according to the invention is shown schematically in FIGS. 6 and 7.

Example 1

Figure 5:
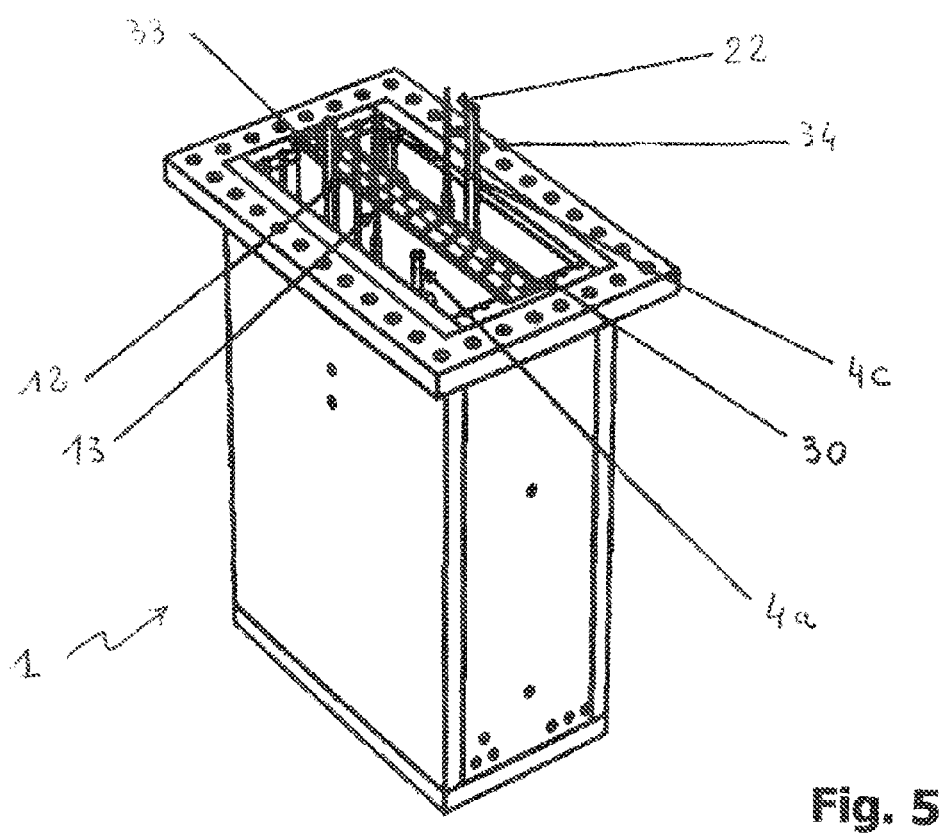
FIG. 5 is a perspective view from above of a reactor according to the invention.

The bioelectrochemical reactor 1 according to the invention, shown schematically in FIGS. 5 and 6, has been designed to replicate industrial conditions. This reactor comprises three compartments separated by two ion exchange membranes: an anode compartment 11 that contains two bioanodes 12 and 13 (which are electrically connected to the outside of the reactor). This compartment is separated by a cation exchange membrane 31 from an inter-membrane compartment 30 which is itself separated by an anion exchange membrane 32 from the cathode compartment 21 that contains the biocathode 22. The volumes of these three compartments are 5.25 L, 2 L and 5.25 L, respectively.

The size of each bioanode 12, 13 is 30×30 cm and it is less than 1 cm thick. The active areas of these two bioanodes is thus 0.36 m², if the four faces of the two bioanodes are considered. The biocathode 22 comprises a volume of 1.2 L of carbon grains, which have an active area of approximately 3 m², i.e. of the order of 10 times the total active area of the bioanodes.

These bioelectrodes are connected to a potentiostat (Bio-Logic®, France, VMP3 not shown, controlled by EC-Lab software), a potential difference of 1.1 V being imposed between the bioanodes and the biocathode.

Reference electrodes 33, 34 may be present in the anode 11 and/or cathode 12 compartments, respectively. In an industrial-scale reactor, these reference electrodes may be absent.

The cathode electrolyte 24 is BMP medium modified with 30 g/L of $NaHCO_3$. The basic anode electrolyte 14 is composed of 12.5 g/L of $Na_2HPO_4 \cdot 7H_2O$, 3 g/L of $KH_2PO_4$, 0.5 g/L of NaCl, 1 g/L of $NH_4Cl$ and 30 g/L of $NaHCO_3$. The electrolyte of the inter-membrane compartment 30 is composed of 35 g/L of KCl and 32.6 g/L of $KH_2PO_4$.

The pH of the anode electrolyte is kept at 7 by automatically injecting a $K_2CO_3$ solution into the anode compartment. The biowaste used is hydrolysates, highly loaded with organic matter, for example the COD value of which is between 100 and 150 g/L. These hydrolysates are introduced into the anode electrolyte by injecting a volume of 10 to 20 mL, either daily or when the anode current drops below approximately 0.5 A/m².

A device (not shown) for collecting the molecules synthesized may be connected to the inter-membrane compartment.

A slight overpressure (for example 20-30 mbar) may be maintained in the gas space of the anode and cathode compartments, preventing air from entering these compartments.

Preparation of Inoculum for the Biocathode

In the case of application of the method of the invention to the electrosynthesis of organic acids or alcohols, the inoculum for the biocathode 22 may be prepared from an anaerobic digester sludge. The preparation consists in applying treatments to, on the one hand, inactivate methanogenic microorganisms which compete with the desired reaction and, on the other hand, to enrich the sludge with microorganisms of interest.

The first step consists in heat-treating the inoculum (at 90° C. for 20 minutes) which results in the methanogens being inactivated.

The second step consists in enriching the sludge with microorganisms of interest by adding hydrogen and carbon dioxide in a closed flask in batch mode. This operation may be repeated twice. The microorganisms of interest here comprise bacteria capable of using the electrons or hydrogen generated at the cathode to synthesize the desired compounds (organic acids or alcohols).

The culture resulting from this enrichment may be used directly and introduced into the cathode compartment 21 upon starting the reactor.

Example 2—Regeneration of a Bioanode

The reactor, such as described in example 1, was put into operation for a period of 140 days. A potential difference of 0.9 V was applied between, on the one hand, the bioanodes that are electrically connected to each other (arranged in parallel) and, on the other hand, the biocathode.

In order to quantify the activity of a bioanode, the most commonly used method is to measure the maximum current density that it is capable of producing in the presence of an organic substrate. The current density at the bioanodes was thus tracked as a function of time (see the curve in FIG. 7 showing the current density as a solid line).

After approximately 18 days, a decrease in this current density was observed, a sign of aging of the bioanodes (range A-A in FIG. 7). One of its bioanodes was then regenerated (arrow R) according to the following method:

The frame 17 and the current collector 16 of one of the removable bioanodes were removed from the anode compartment 11 by sliding within one of the slots 20 (see FIG. 6) cleaned using a detergent and then dried, the grid 18 made of stainless steel and the carbon fabrics 15 were replaced with new materials.

The new, renewed bioanode was then put back in the position closest to the membrane 31, the other bioanode having been moved into the other slot, closer to the outer wall of the reactor.

It can clearly be seen that after this replacement of one of the bioanodes, activity returns for at least forty days. Aging is then observed again from the peak B-B in FIG. 7. The second bioanode may then be replaced as presented above for the first bioanode.

The invention claimed is:

1. A bioelectrochemical reactor comprising:
    an anode compartment comprising at least two anodes, called bioanodes, and an anode electrolyte comprising anodic electroactive microorganisms,
    a cathode compartment comprising at least one cathode, called a biocathode, and a cathode electrolyte comprising cathodic electroactive microorganisms,
    the anode compartment being separated from the cathode compartment by, running from the anode compartment to the cathode compartment, a cation exchange membrane and an anion exchange membrane, said cation and anion exchange membranes being separated from one another by an inter-membrane compartment,
    means for applying a potential difference between the bioanodes connected to one another and the one or more biocathodes,
    the bioanodes and one or more biocathodes having active areas such that the total active area of the one or more biocathodes is greater than the total active area of the two bioanodes.

2. The bioelectrochemical reactor as claimed in claim 1, wherein the bioanodes are removable.

3. The bioelectrochemical reactor as claimed in claim 1, wherein said reactor is a microbial electrosynthesis reactor, the anode compartment comprising one or more ports for injecting organic carbonaceous substrate, the cathode compartment comprising one or more ports for injecting $CO_2$ or for introducing an organic or inorganic carbon source and the inter-membrane compartment comprising a device for extracting the molecules synthesized within said reactor.

4. The bioelectrochemical reactor as claimed in claim 3, wherein the organic carbonaceous substrate is at least one organic biowaste hydrolysate.

5. The bioelectrochemical reactor as claimed in claim 1, wherein the biocathode is a three-dimensional electrode.

6. The bioelectrochemical reactor as claimed in claim 5, wherein the biocathode comprises a granular material or takes the general form of a lattice.

7. The bioelectrochemical reactor as claimed in claim 5, wherein the biocathode comprises carbon grains arranged in a container made of stainless steel.

8. The bioelectrochemical reactor as claimed in claim 1, wherein the bioanodes take the general form of a panel.

9. The bioelectrochemical reactor as claimed in claim 8, wherein the bioanodes are formed of a carbon fabric or felt, held in a metal frame.

10. The bioelectrochemical reactor as claimed in claim 9, wherein the metal frame is a frame made of stainless steel.

11. The bioelectrochemical reactor as claimed in claim 1, wherein said reactor comprises means for regulating the pH of the anode and/or the temperature.

12. The bioelectrochemical reactor as claimed in claim 8, wherein the panel is a planar or rounded panel.

13. A method for regenerating the activity of the bioanodes of the reactor as claimed in claim 2, comprising:
- a step of removing at least one of the bioanodes from the anode compartment, it being understood that at least one bioanode is left in the anode compartment,
- a step of cleaning, outside the reactor, said one or more removed bioanodes, then reintroducing them into the anode compartment,
- the reactor being kept in operation by applying a potential difference between the biocathode and the remaining bioanode in the anode compartment.

14. A method for regenerating the activity of the bioanodes of the reactor as claimed in claim 2, comprising:
- replacing at least one of the bioanodes of the anode compartment with an anode not colonized by electroactive microorganisms, it being understood that at least one bioanode is left in the anode compartment,
- the reactor being kept in operation by applying a potential difference between the biocathode and the remaining bioanode in the anode compartment.

15. A method for electrosynthesis of organic acids and/or alcohols, said method comprising the step of:
- introducing organic waste into the bioelectrochemical reactor as claimed in claim 1.

16. The use method as claimed in claim 15, wherein the organic waste is chosen from: biowaste hydrolysates, hydrolyzed sludge from wastewater treatment plants, various organic liquid fractions from wastewater treatment plants, municipal wastewater after primary settling, organic industrial waste, agro-food waste, digestates from wastewater treatment plants, or a mixture of a plurality thereof.

\* \* \* \* \*